United States Patent
Simpson et al.

(10) Patent No.: US 9,872,713 B2
(45) Date of Patent: Jan. 23, 2018

(54) SPINAL CORRECTION SYSTEM AND METHOD

(71) Applicant: Warsaw Orthopedic, Inc., Warsaw, IN (US)

(72) Inventors: Joshua W. Simpson, Collierville, TN (US); Dennis G. Crandall, Mesa, AZ (US); Jason M. May, Corodva, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 67 days.

(21) Appl. No.: 14/104,131

(22) Filed: Dec. 12, 2013

(65) Prior Publication Data

US 2015/0164561 A1 Jun. 18, 2015

(51) Int. Cl.
*A61B 17/70* (2006.01)
*A61B 17/00* (2006.01)

(52) U.S. Cl.
CPC ...... *A61B 17/7083* (2013.01); *A61B 17/7002* (2013.01); *A61B 17/7032* (2013.01); *A61B 17/7086* (2013.01); *A61B 2017/00004* (2013.01)

(58) Field of Classification Search
CPC ............ A61B 17/7002; A61B 17/7022; A61B 17/7053; A61B 17/7083
USPC .................................................. 606/263, 86 A
See application file for complete search history.

(56) References Cited

U.S. PATENT DOCUMENTS

| 5,782,831 | A | * | 7/1998 | Sherman | A61B 17/7079 606/103 |
| 2007/0233066 | A1 | * | 10/2007 | Rezach | A61B 17/7037 606/252 |
| 2011/0270314 | A1 | * | 11/2011 | Mueller et al. | 606/264 |
| 2013/0072983 | A1 | * | 3/2013 | Lindquist | A61B 17/7049 606/278 |
| 2013/0268005 | A1 | * | 10/2013 | Rezach et al. | 606/263 |
| 2014/0148854 | A1 | * | 5/2014 | Carlson et al. | 606/254 |

FOREIGN PATENT DOCUMENTS

WO    WO 2013070628 A1 *  5/2013

OTHER PUBLICATIONS

Office Action issued by German Patent and Trademark Office on Apr. 3, 2017 in German Application No. 10 2014 118 068.2.

* cited by examiner

*Primary Examiner* — Nicholas Plionis

(57) ABSTRACT

A spinal construct includes a spinal rod and a reduction member connected with the spinal rod and engageable with a tether connected to the spinal rod. The reduction member is translatable relative to the tether to dispose the spinal rod with a fastener configured for penetrating tissue. Systems and methods are disclosed.

20 Claims, 7 Drawing Sheets

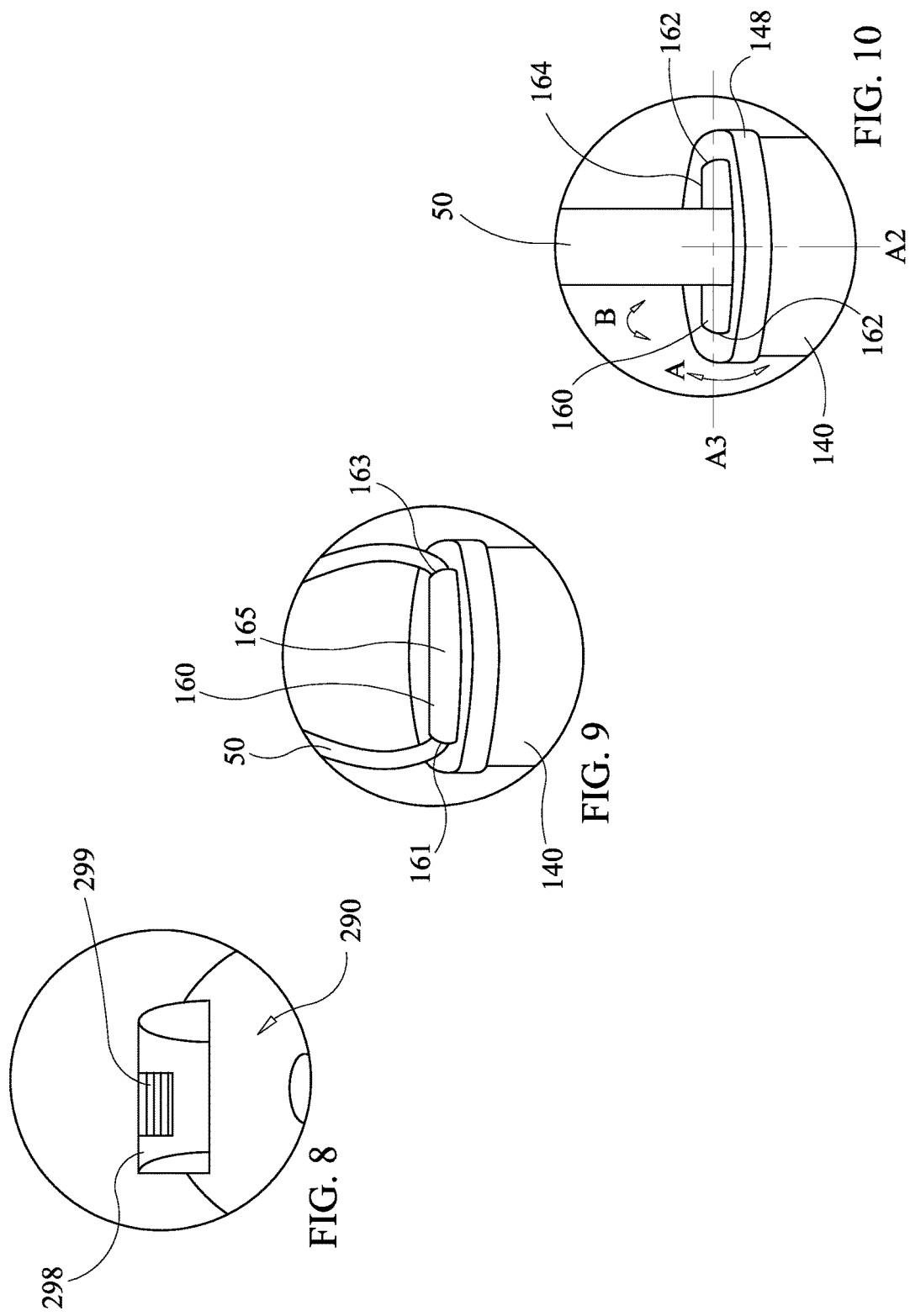

SPINAL CORRECTION SYSTEM AND METHOD

TECHNICAL FIELD

The present disclosure generally relates to medical devices for the treatment of musculoskeletal disorders, and more particularly to a surgical system for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. Correction treatments used for positioning and alignment of vertebrae may employ implants, such as, for example, spinal constructs. The spinal constructs, which may include rods and bone screws, are manipulated with surgical instruments for engagement with vertebrae to position and align one or more vertebrae. This disclosure describes an improvement over these prior art technologies.

SUMMARY

In one embodiment, a spinal construct is provided. The spinal construct includes a spinal rod and a reduction member connected with the spinal rod and engageable with a tether connected to the spinal rod. The reduction member is translatable relative to the tether to dispose the spinal rod with a fastener configured for penetrating tissue. In some embodiments, systems and methods are provided.

BRIEF DESCRIPTION OF THE DRAWINGS

The present disclosure will become more readily apparent from the specific description accompanied by the following drawings, in which:

FIG. 8 is a detail view of components of the system shown in FIG. 7;

FIG. 9 is a detail view of components of the system shown in FIG. 7;

FIG. 10 is a detail view of components of one embodiment of a system in accordance with the principles of the present disclosure.

DETAILED DESCRIPTION

Figure 1:
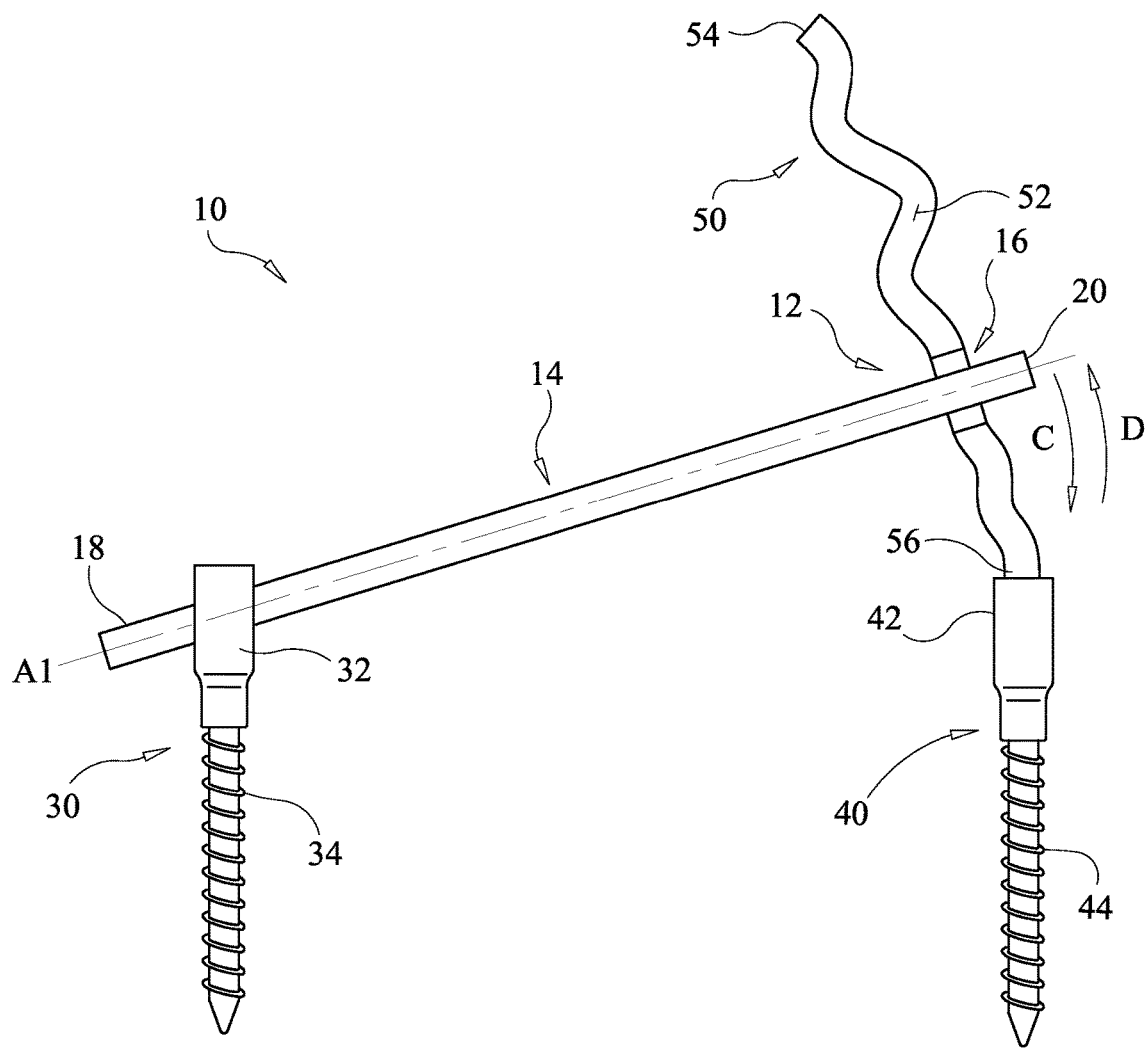
FIG. 1 is a side view of components of one embodiment of a system in accordance with the principles of the present disclosure.
Figure 2:
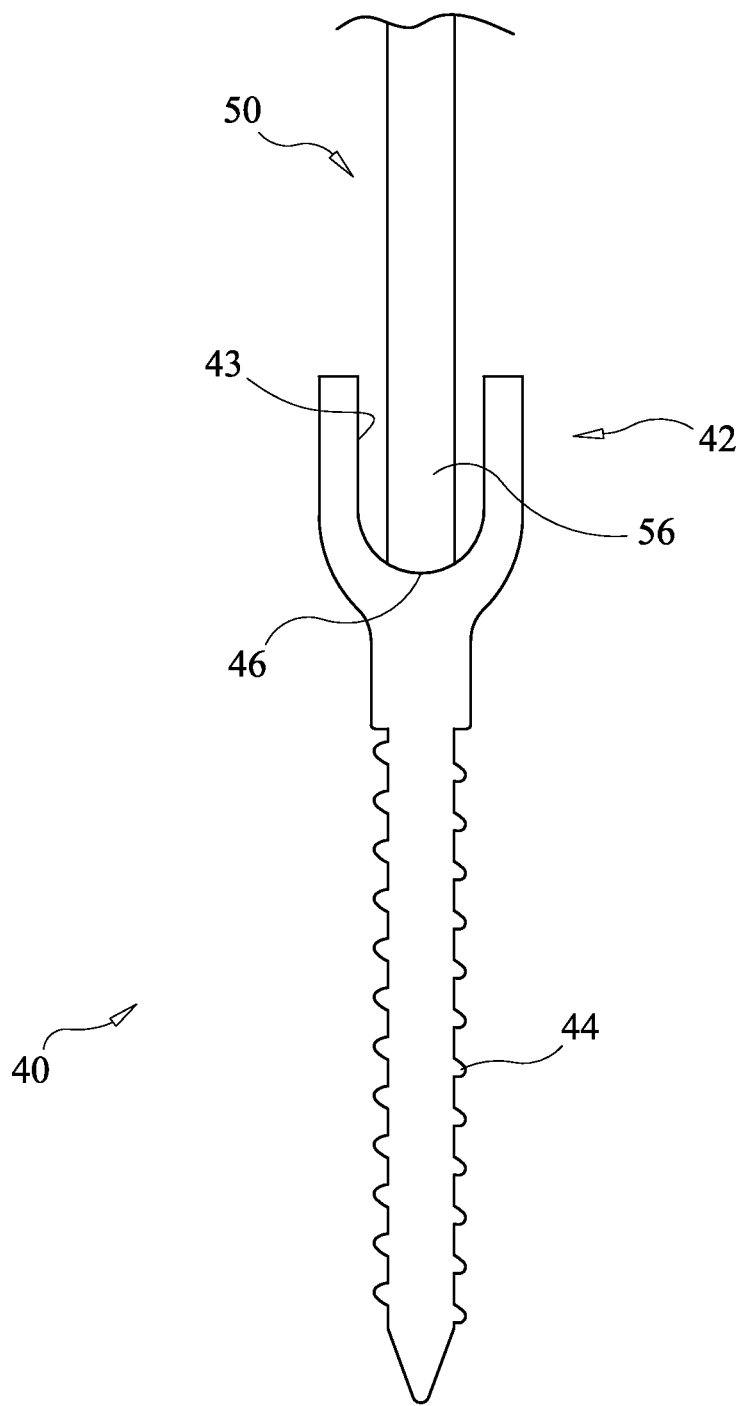
FIG. 2 is a side cross section view of components of the system shown in FIG. 1.

The exemplary embodiments of the system and related methods of use disclosed are discussed in terms of medical devices for the treatment of musculoskeletal disorders and more particularly, in terms of a surgical system and method for correction of a spine disorder.

In one embodiment, a surgical system is provided including a reduction mechanism having a long throw. In one embodiment, the reduction mechanism has variability in a direction of the throw. In one embodiment, the surgical system includes a tether coupled to spinal tissue via a bone fastener, such as, for example, a bone screw and a rod, such as, for example, a spinal rod. The spinal rod can be reduced down to the spinal tissue by pulling the spinal rod down the tether. In one embodiment, a one way crimp can be used to prevent the spinal rod from backing out of the bone screw. In one embodiment, the surgical system is used for a large or hyperkyphosis or a spondylolisthesis reduction. In one embodiment, the surgical system can be used for a translational correction technique. In one embodiment, the crimp is lockable with the bone screw for final tightening and can be a permanently implantable component of the surgical system. In one embodiment, the tether is used in a spondylolisthesis reduction to pull vertebrae towards the spinal rod.

In one embodiment, a surgical system is provided including a bone fastener, such as, for example, a pedicle screw, a rod attachment, such as, for example, connectors, a tensioning device, and a longitudinal element, such as, for example, a spinal rod. In one embodiment, the pedicle screw includes a head having two loops for attachment of two tethers, such as, for example, 4 millimeter (mm) wide synthetic polyester fiber tape. In one embodiment, the pedicle screw is connected to one tether. In one embodiment, the pedicle screw includes a head having an anchor connected to the tether and being pivotable relative to the pedicle screw. In one embodiment, the connector is engaged to the spinal rod and the tether to couple the spinal rod with the tether. In one embodiment, the connector locks the tape on the rod. In one embodiment, the connector is an open connector. In one embodiment, the connector locks the 4 mm tape to the spinal rod. In one embodiment, the tensioning device pulls the spinal rod along the tape towards the pedicle screw. In one embodiment, the tensioning device includes a dispensing gun type configuration.

In some embodiments, one or all of the components of the spinal correction system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the appended claims, in some embodiments, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

The following discussion includes a description of a system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a system, such as, for example, a spinal correction system 10 in accordance with the principles of the present disclosure.

The components of system 10 can be fabricated from biologically acceptable materials suitable for medical applications, including metals, synthetic polymers, ceramics, bone material, tissue and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a spinal construct 12 comprising an implant, such as, for example, a spinal rod 14 and a reduction member 16 connected with spinal rod 14. Reduction member 16 reduces spinal rod 14 along a tether 50 into a head 42 of a fastener, such as, for example, a bone screw 40 in connection with treatment of a spinal deformity. Spinal rod 14 includes an end 18 and an end 20 defining a longitudinal axis A1 therebetween. End 18 is configured for attachment with a fastener, such as, for example, a bone screw 30 fixed with vertebrae and end 20 is configured for connection with bone screw 40 fixed with vertebrae such that movement of vertebrae is resisted and/or prevented therebetween. Spinal rod 14 has an arcuate cross section configuration and is substantially cylindrical. In some embodiments, spinal rod 14 has a variously configured cross section configuration, such as, for example, round, oval, oblong, square, triangular, rectangular, irregular, uniform, non-uniform, consistent, and/or variable. In one embodiment, spinal rod 14 is disposed to extend along an axial plane, such as for example, a sagittal plane of a body of a patient. In some embodiments, system 10 may include one or a plurality of spinal rods 14. In some embodiments, one or a plurality of spinal rods 14 may be disposed in various relative orientations, such as, for example, side-by-side, parallel, transverse, perpendicular or angular and/or be disposed to extend along substantially coronal, sagittal and transverse planes of a body.

System 10 includes tether 50. In some embodiments, tether 50 includes tape. Tether 50 extends between an end 54 and an end 56 connected with head 42 of bone screw 40. In one embodiment, tether 50 comprises a loop encircled about spinal rod 14. In some embodiments, tether 50 has a flexible configuration, which includes movement in a lateral or side to side direction and prevents expanding and/or extension in an axial direction upon fixation with vertebrae, as described herein. In some embodiments, all or only a portion of tether 50 may have a semi-rigid, rigid, flexible or elastic configuration, and/or have elastic and/or flexible properties such as the elastic and/or flexible properties corresponding to the material examples described above such that tether 50 provides a selective amount of expansion and/or extension in an axial direction. In some embodiments, tether 50 may be compressible in an axial direction. Tether 50 can include a plurality of separately attachable or connectable portions or sections, such as bands or loops, or may be monolithically formed as a single continuous element.

Tether 50 has an outer surface 52 and a uniform thickness/diameter. In some embodiments, outer surface 52 may have various surface configurations, such as, for example, rough, threaded for connection with surgical instruments, arcuate, undulating, porous, semi-porous, dimpled, polished and/or textured. In some embodiments, the thickness defined by tether 50 may be uniformly increasing or decreasing, or have alternate diameter dimensions along its length. In some embodiments, tether 50 may have various cross section configurations, such as, for example, oval, oblong, triangular, rectangular, square, polygonal, irregular, uniform, non-uniform, variable and/or tapered.

In some embodiments, tether 50 may have various lengths. In some embodiments, tether 50 may be braided, such as a rope, or include a plurality elongated elements to provide a predetermined force resistance. In some embodiments, tether 50 may be made from autograft and/or allograft, as described herein, and be configured for resorbable or degradable applications.

In some embodiments, tether 50 may include one or a plurality of flexible wires, staples, cables, ribbons, artificial and/or synthetic strands, rods, plates, springs, and combinations thereof. In one embodiment, tether 50 is a cadaver tendon. In one embodiment, tether 50 is a solid core. In one embodiment, tether 50 is tubular.

System 10 includes bone screw 30 attached with end 18 of spinal rod 14 and connected with spinal tissue, such as, for example, vertebrae. Bone screw 30 comprises a first portion, such as, for example, a head 32 and a second portion, such as, for example, an elongated shaft 34 configured for penetrating tissue. Head 32 defines an inner surface defining a cavity, such as, for example, a U-shaped implant cavity, configured for disposal of end 18 of spinal rod 14.

Shaft 34 has a cylindrical cross section configuration and includes an outer surface having an external threaded form. In some embodiments, the thread form may include a single thread turn or a plurality of discrete threads. In some embodiments, other engaging structures may be located on shaft 34, such as, for example, a nail configuration, barbs, expanding elements, raised elements and/or spikes to facilitate engagement of shaft 34 with tissue, such as, for example, vertebrae.

In some embodiments, all or only a portion of shaft 34 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 34 may include one or a plurality of openings. In some embodiments, all or only a portion of the outer surface of shaft 34 may have alternate surface configurations to enhance fixation with tissue such as, for example, rough, arcuate, undulating, mesh, porous, semi-porous, dimpled and/or textured. In some embodiments, all or only a portion of shaft 34 may be disposed at alternate orientations, relative to axis A1, such as, for example, transverse, perpendicular and/or other angular orientations such as acute or obtuse, co-axial and/or may be offset or staggered. In some embodiments, all or only a portion of shaft 34 may be cannulated.

System 10 includes bone screw 40, similar to bone screw 30 described herein. Bone screw 40 is configured for engagement with spinal tissue spaced from bone screw 30. Bone screw 40 is connected with end 56 of tether 50 and connectable with end 20 of spinal rod 14 upon reduction of spinal rod 14 along tether 50 and into engagement with bone screw 40. Bone screw 40 includes a first portion, such as, for example, head 42, and a second portion, such as, for example, a shaft 44 configured for penetrating engagement with tissue, such as, for example, spinal tissue. Head 42 includes a pair of arms defining a U-shaped implant cavity 43 configured for disposal of spinal rod 14. End 56 of tether 50 may be monolithically formed with, integrally connected or attached with fastening elements to head 42 of bone screw 40.

Bone screw 40 includes an engagement part 46 disposed at a distal end of head 42. In some embodiments, engagement part 46 is disposed with various portions of head 42 of bone screw 40, such as, for example, spaced apart arms, within U-shaped implant cavity 43, or shaft 44. Engagement part 46 has a semi-circular configuration and is configured for looping tether 50 thereabout such that spinal rod 14 is translatable along tether 50 into implant cavity 43. In some embodiments, engagement part 46 is variously configured, such as, for example, oval, oblong, triangular, rectangular, square, polygonal, irregular, uniform, non-uniform, horseshoe shape, U-shape, kidney bean shape, variable and/or tapered. In some embodiments, tether 50 is connected to head 42 by various fastening mechanisms, such as, for example, buttons, clips, snaps, friction fittings, compressive fittings, expanding rivets, staples, nails and/or adhesives.

In some embodiments, one or a plurality of bone screws may be connected with tether 50. In some embodiments, system 10 can include one or a plurality of bone screws, such as those described herein and/or fixation elements, which may be employed with a single vertebral level or a plurality of vertebral levels. In some embodiments, the bone screws may be engaged with vertebrae in various orientations, such as, for example, series, parallel, offset, staggered and/or alternate vertebral levels. In some embodiments, the bone screws and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. These bone screws and/or fixation elements may be coated with an osteoinductive or osteoconductive material to enhance fixation, and/or include one or a plurality of therapeutic agents.

Reduction member 16 is connected with spinal rod 14 and engageable with tether 50 to connect tether 50 with spinal rod 14. Reduction member 16 has a rectangular configuration. In some embodiments, reduction member 16 is variously configured, such as, for example, cylindrical, oval, oblong, tapered, uniform, non-uniform, arcuate, round, triangular, square, kidney-bean shaped, polygonal, irregular, consistent and/or variable. Reduction member 16 includes an inner surface 66 defining a cavity 68 extending through its thickness configured for disposal of tether 50. Reduction member 16 is translatable relative to and along tether 50 to dispose spinal rod 14 with implant cavity 43 of bone screw 40. Reduction member 16 is movable, such as, for example, translatable, in a first direction, as shown by arrow C in FIG. 1. Translation of reduction member 16 is resisted and/or prevented in a second direction, as shown by arrow D in FIG. 1. Reduction member 16 is movable in the first direction relative to tether 50 to translate spinal rod 14 adjacent bone screw 40. In some embodiments, the direction of movement of member 16 relative to tether 50 can include linear, arcuate, staggered and/or offset translation. In some embodiments, translation of reduction member 16 is selectively resisted and/or prevented in the second direction.

Figure 3:
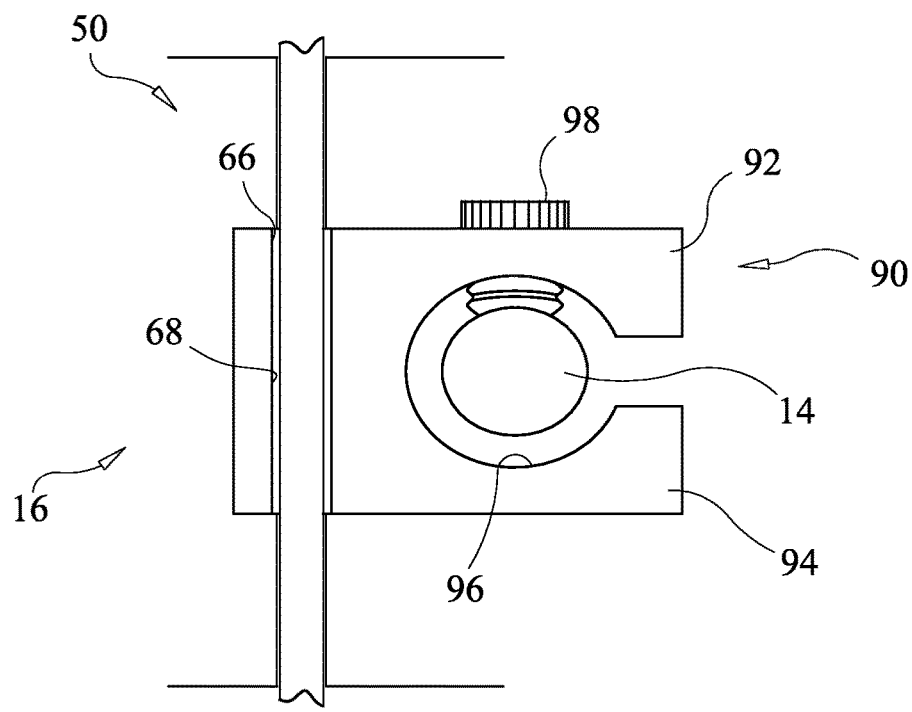
FIG. 3 is a side cross section view of components of the system shown in FIG. 1.

Reduction member 16 includes a connector 90, as shown in FIG. 3, connected with spinal rod 14. Connector 90 couples spinal rod 14 with tether 50 such that spinal rod 14 moves with reduction member 16. Connector 90 includes an arcuate arm 92 and an arcuate arm 94 together defining a cavity 96 configured for disposal of spinal rod 14. In some embodiments, arms 92, 94 are relatively movable to expand and/or contract cavity 96. Connector 90 includes a coupling member, such as, for example, a screw 98. Screw 98 is threadably engaged with at least one of arms 92, 94. With spinal rod 14 disposed in cavity 96, screw 98 is axially translated into engagement with spinal rod 14 such that spinal rod 14 is captured in cavity 96 between arms 92, 94. In some embodiments, connector 90 is integrally connected to or monolithically formed with reduction member 16. In one embodiment, end 20 of spinal rod 14 includes a bore (not shown) extending through its thickness configured for disposal of tether 50 such that tether 50 is translatable through the bore.

Figure 4:
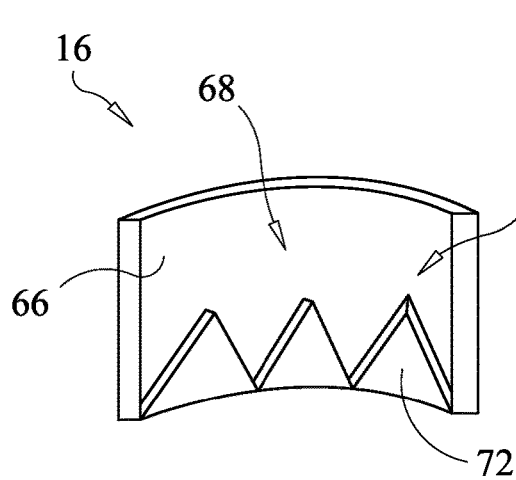
FIG. 4 is a cross section view of components of the system shown in FIG. 1.

In one embodiment, as shown in FIG. 4, reduction member 16 comprises a crimp 70 that resists movement of reduction member 16 in at least one direction, such as, for example, in the direction shown by arrow D. Crimp 70 includes inner surface 66, which has at least one penetrating element, such as, for example, teeth 72, engageable with tether 50 to resist movement in the at least one direction. Teeth 72 extend from inner surface 66 into cavity 68 at an angular orientation such that teeth 72 penetrate tether 50 when crimp 70 moves in the second direction. In some embodiments, teeth 72 may be disposed at alternate orientations, relative to inner surface 66 of crimp 70, such as, for example, transverse, and/or other angular orientations such as acute or obtuse, co-axial and/or may be offset or staggered. In some embodiments, crimp 70 may include one or a plurality of penetrating elements. In some embodiments, teeth 72 can be variously configured, such as, for example, nails, serrated, textured, staggered, uneven, undulating, smooth, barbs and/or raised elements to facilitate mating with tether 50 during movement of crimp 70 in the second direction.

Figure 5:
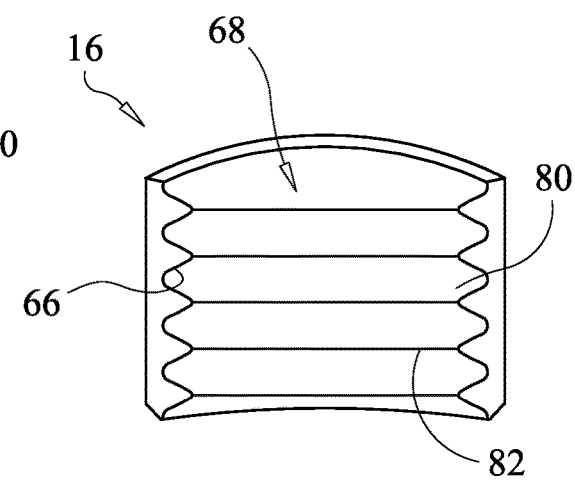
FIG. 5 is a cross section view of components of the system shown in FIG. 1.

In one embodiment, as shown in FIG. 5, reduction member 16 comprises a ratchet 80 engageable with tether 50. Ratchet 80 includes a series of linear racks 82 extending circumferentially from inner surface 66 into cavity 68 at an angular orientation such that racks 82 engage outer surface 52 of tether 50 when ratchet 80 moves in the second direction. Racks 82 have a tapered configuration from inner surface 66 towards cavity 68. In some embodiments, racks 82 are variously configured, such as, for example, oval, oblong, triangular, rectangular, square, polygonal, irregular, uniform, non-uniform, variable and/or tapered. In some embodiments, tether 50 includes an engagement feature, such as, for example, a pawl (not shown) configured for engaging racks 82 during movement of ratchet 80 in the second direction.

In operation, bone screw 40 is connected with end 56 of tether 50. Bone screw 40 is connected with spinal tissue, such as, for example, a selected first vertebral level, in a configuration for penetrating the first vertebral level. Bone screw 30 is connected with spinal tissue, such as, for example, a second vertebral level, spaced from the first vertebral level. End 18 of spinal rod 14 is attached with bone screw 30 fixed with the second vertebral level and end 20 of spinal rod 14 is captured in cavity 96 of connector 90. Tether 50 is disposed in cavity 68 of reduction member 16 such that spinal rod 14 is connected with tether 50. Tension is applied to tether 50 and reduction member 16 is translated relative to tether 50, in the direction shown by arrow C in FIG. 1, translating end 20 of spinal rod 14 along tether 50 to reduce spinal rod 14 with U-shaped implant cavity 43 of bone screw 40 and/or an adjacent bone screw. In some embodiments, the translation of spinal rod 14 along tether 50 applies a corrective force on vertebrae to selectively align the vertebrae. In some embodiments, tether 50 is detached from bone screw 40 upon disposal of end 20 of spinal rod 14 with bone screw 40.

In assembly, operation and use, a surgical system, including spinal correction system 10, similar to the systems and methods described herein, is employed with a surgical correction procedure. For example, spinal correction system 10 may be employed in surgical procedures for treating disorders of the spine, such as, for example, abnormal curvatures of a spine including hyper-kyphosis.

Figure 6:
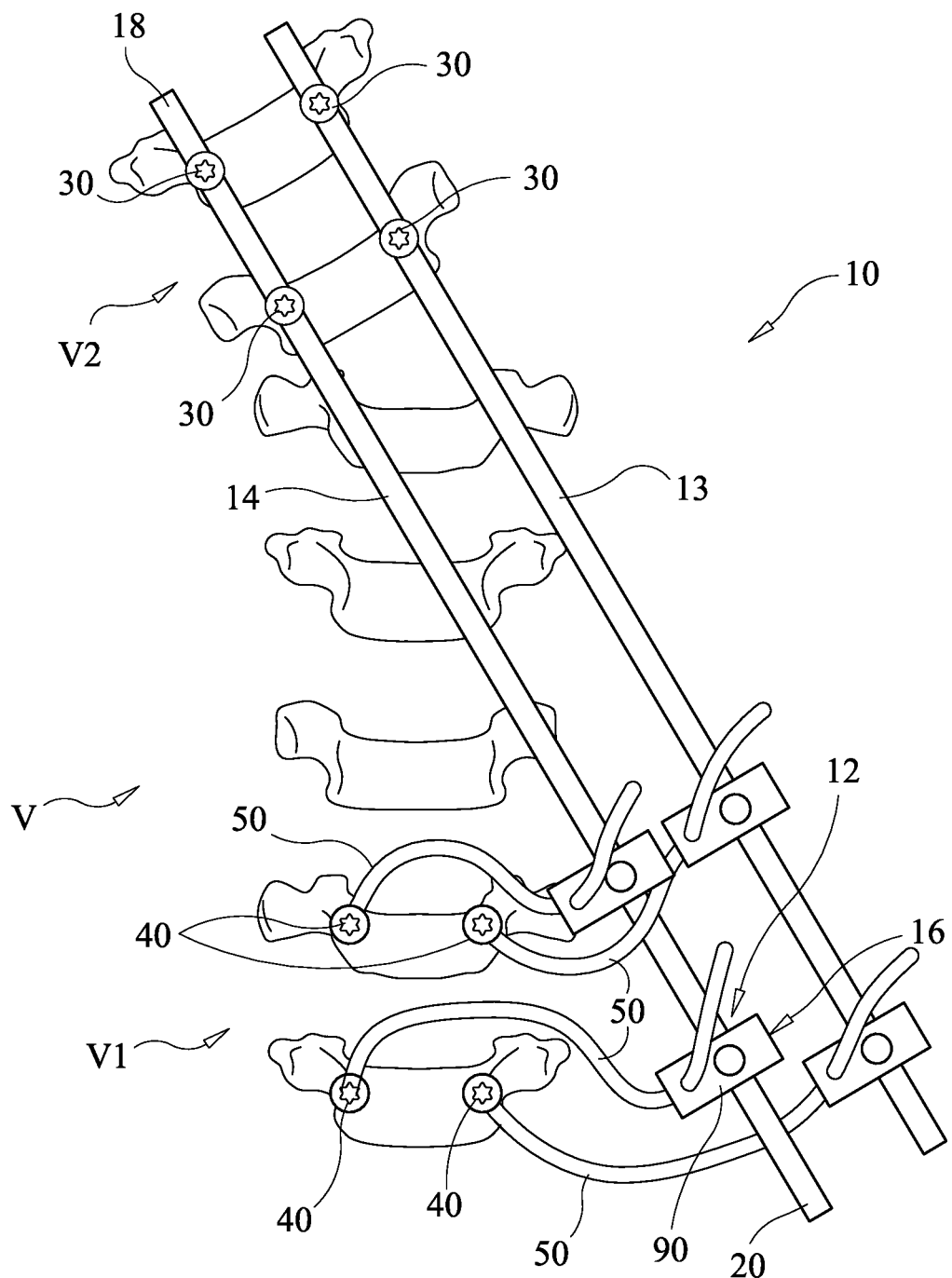
FIG. 6 is a plan view of components of one embodiment of a system in accordance with the principles of the present disclosure disposed with vertebrae.

In some embodiments, one or all of the components of spinal implant system 10 can be delivered or implanted as a pre-assembled device or can be assembled in situ. The components of spinal correction system 10 may be completely or partially revised, removed or replaced. For example, spinal correction system 10 can be employed with a surgical correction treatment of an applicable condition or injury of an affected section of a spinal column and adjacent areas within a body, such as, for example, vertebrae V, as shown in FIG. 6.

In use, to treat a selected section of vertebrae V, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

One or a plurality of incisions are made in the body of a patient and a cutting instrument (not shown) creates one or a plurality of surgical pathways and/or openings for implantation of components of spinal correction system 10. A preparation instrument (not shown) can be employed to prepare tissue surfaces of vertebrae V, as well as for aspiration and irrigation of a surgical region.

Pilot holes (not shown) are made bilaterally in selected levels of vertebrae V, for example, vertebrae V1, V2 for receiving bone screws 30, 40. Shafts 34, 44 are inserted, drilled or otherwise fixed to vertebrae V1, V2 to attach bone screws 30, 40 with vertebrae V. Each of bone screws 40 are connected with a separate tether 50.

Spinal rod 14 and a spinal rod 13, similar to spinal rod 14 described herein, are delivered along the surgical pathway to the surgical site adjacent vertebrae V. In some embodiments, spinal rods 13, 14 and spinal construct 12 and/or bone screws 30, 40 can be delivered or implanted as pre-assembled components or can be assembled in situ. Spinal rods 13, 14 are positioned for disposal within U-shaped implant cavities of bone screws 30 to connect spinal rods 13, 14 with bone screws 30. In some embodiments, spinal rods 13, 14 may be attached with vertebrae V with a plurality of bone fasteners over a plurality of vertebral levels. Spinal rods 13, 14 are disposed with vertebrae in a side-by-side orientation. In some embodiments, spinal rods 13, 14 are oriented in various configurations, as described herein.

Set screws (not shown) are torqued and threaded with threads of the U-shaped implant cavities of selected bone screws 30 to secure spinal rods 13, 14 with vertebrae V2. For example, the set screws capture end 18 of spinal rod 14 within the U-shaped implant cavities of bone screws 30.

Bone screw 40 is connected with end 56 of tether 50. End 20 of spinal rod 14 is captured in cavity 96 of connector 90. Tether 50 is disposed in cavity 68 of reduction member 16 such that spinal rod 14 is connected with tether 50. Tension is applied to tether 50 and reduction member 16 is translated relative to tether 50, in the direction shown by arrow C in FIG. 1, translating end 20 of spinal rod 14 along tether 50 to reduce spinal rod 14 with U-shaped implant cavity 43 of bone screw 40 and to dispose rod 14 with screw 40. The translation of spinal rod 14 along tether 50 applies a corrective force on vertebrae V to selectively align vertebrae V. In some embodiments, tether 50 is detached from bone screw 40 upon disposal of end 20 of spinal rod 14 with bone screw 40. In some embodiments, tension is applied to tether 50 and member 16 translates along tether 50 to translate rod 14 and/or draw the receiver of screw 40 up to receive rod 14. In some embodiments, member 16 may reduce rod 14 with screw 40 incrementally or continuously.

In some embodiments, spinal implant system 10 may include a spinal construct comprising one or a plurality of spinal constructs 12 that are each attachable with a selected vertebral level of vertebrae V, or two or more selected vertebral levels of vertebrae V. Spinal correction system 10 accommodates for growth of vertebrae of a selected section of the spine for a correction treatment to treat various spine pathologies, such as, for example, adolescent idiopathic scoliosis and Scheuermann's kyphosis.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal correction system 10 are removed and the incision is closed. Spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

In one embodiment, as shown in FIGS. 7-11, spinal correction system 10, similar to the systems and methods described with regard to FIGS. 1-6, includes a spinal construct 212, similar to spinal construct 12 described with regard to FIGS. 1-6. Spinal construct 212 comprises an implant, such as, for example, spinal rod 14 and a reduction member, such as, for example, a tensioning device 216.

Figure 7:
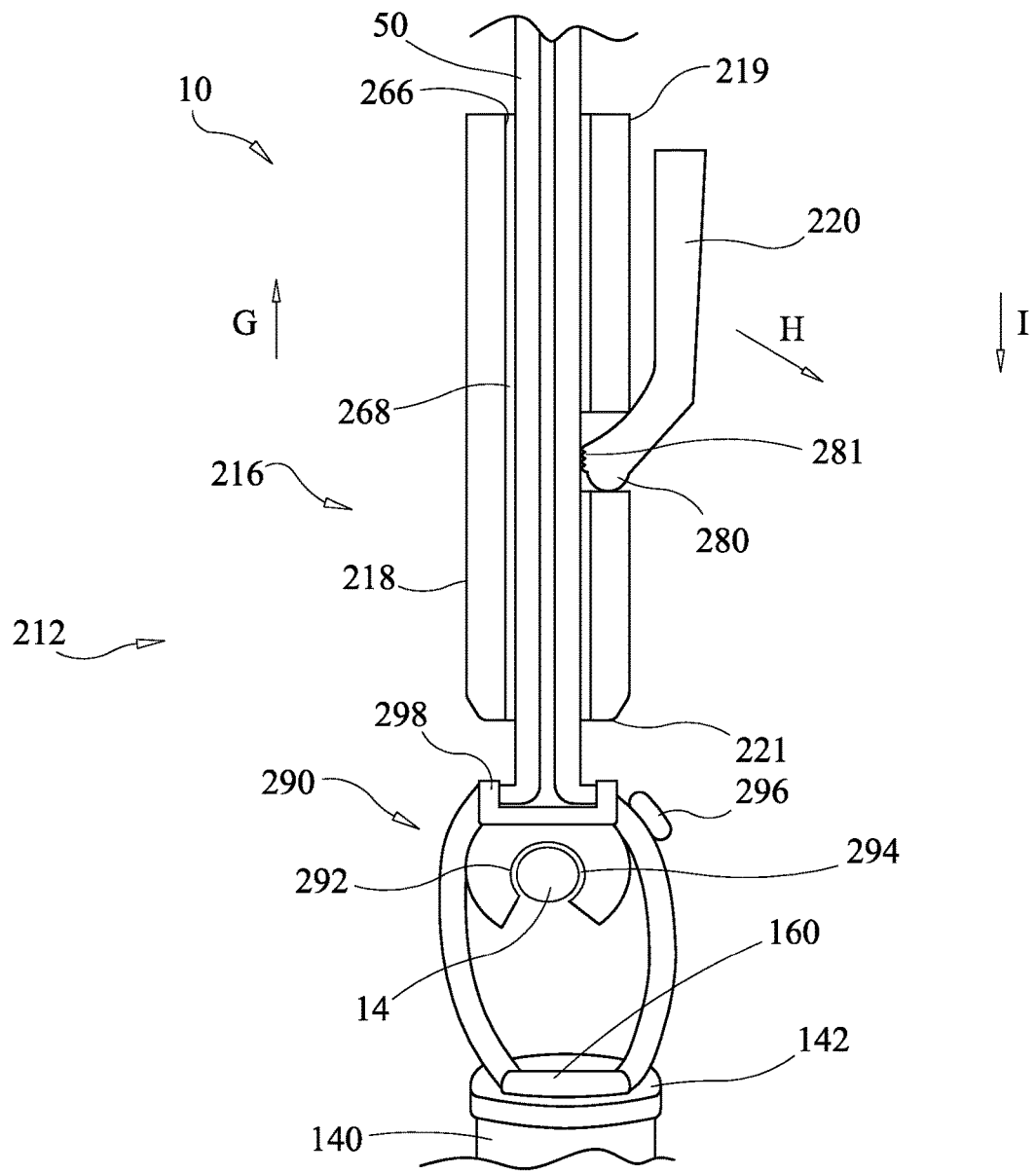
FIG. 7 is a side perspective view, in part cross section, of components of one embodiment of a system in accordance with the principles of the present disclosure.
Figure 11:
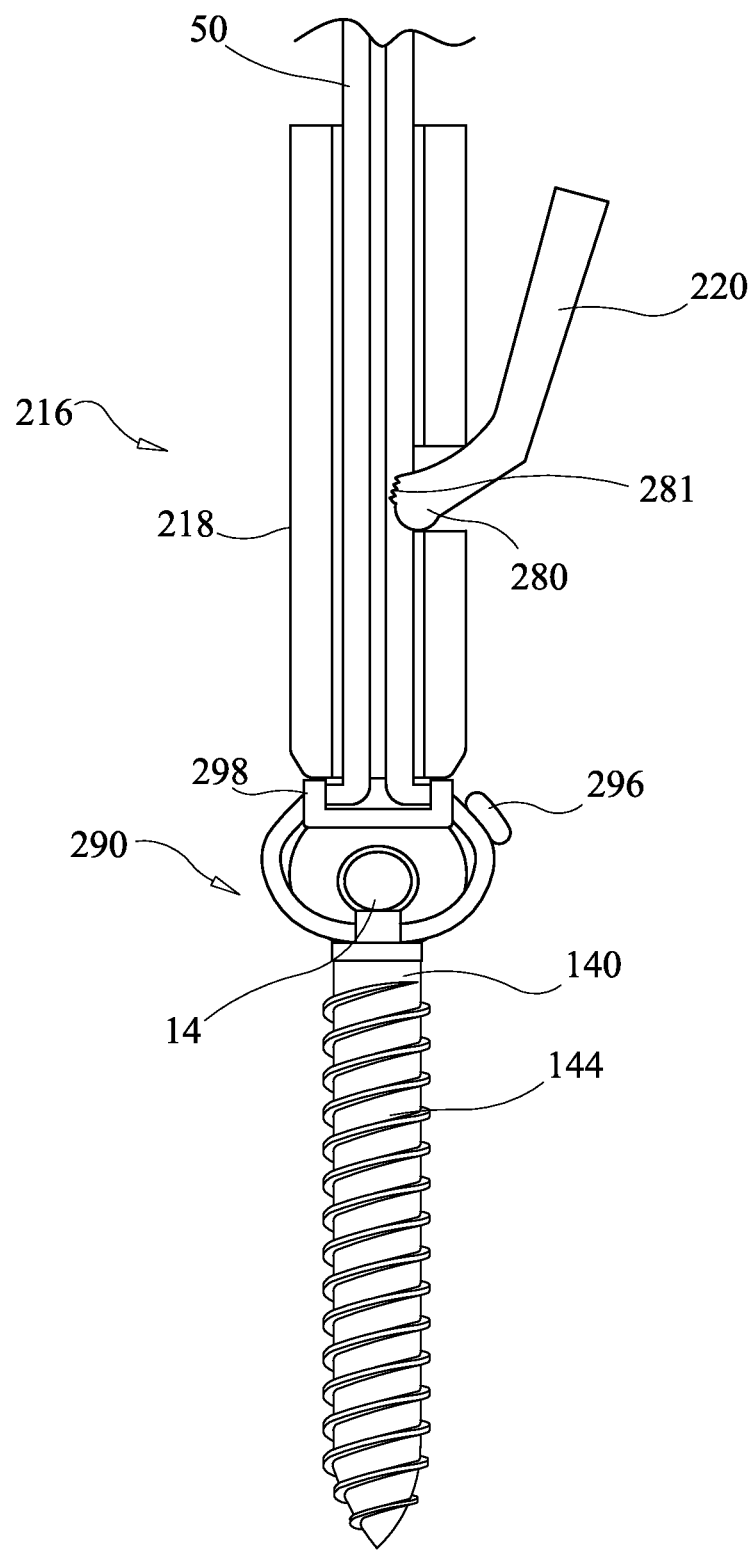
FIG. 11 is a side perspective view, in part cross section, of components of the system shown in FIG. 7.

Tensioning device 216 is connected with spinal rod 14 via a connector and engageable with tether 50. Tensioning device 216 includes a body 218 extending between an end 219 and an end 221. Body 218 has a cylindrical configuration. Body 218 includes an inner surface 266 defining a passageway 268 extending through a length of tensioning device 216 configured for disposal of tether 50. Body 218 includes an arm 220 extending at an angular orientation therefrom. Arm 220 is pivotally connected to body 218 such that arm 220 is pivotable relative to body 218 between a first configuration, as shown in FIG. 7, and a second configuration, as shown in FIG. 11. In some embodiments, arm 220 is resiliently biased to the second configuration. Arm 220 includes a ratchet 280, similar to ratchet 80 described herein, extending into cavity 268 and engageable with tether 50 to resist movement of tensioning device 216 relative to tether 50, in a direction shown by arrow G in FIG. 7. Ratchet 280 includes a series of teeth 281 frictionally engageable with tether 50 to facilitate movement of device 216, in the direction shown by arrow I, as described herein.

The actuation of arm 220 via a force applied to arm 220, in a direction shown by arrow H in FIG. 7, engages teeth 281 of ratchet 280 with tether 50. Tether 50 is drawn through passageway 268 of tensioning device 216, in the direction shown by arrow G, such that tensioning device 216 translates relative to and along tether 50, in the direction shown by arrow I in FIG. 7. Tensioning device 216, similar to reduction member 16 described herein, is translatable relative to tether 50 to dispose spinal rod 14 with a bone screw 140.

Spinal construct 212 comprises a connector, such as, for example, a C-shaped damp 290 connected with spinal rod 14 and engageable with tether 50, similar to connector 90 described herein. C-shaped damp 290 connects spinal rod 14 with tether 50 such that spinal rod 14 is movable along tether 50. C-shaped damp 290 includes an inner surface 292 defining a cavity 294 configured for disposal of spinal rod 14. C-shaped damp 290 includes a locking element, such as, for example, a screw 296. Screw 296 is threadably engaged with C-shaped clamp 290. With spinal rod 214 disposed in cavity 294, screw 296 is translated into engagement with spinal rod 14 such that spinal rod 14 is captured in cavity 294. C-shaped clamp 290 includes a hook portion 298 disposable about tether 50 coupling tether 50 with C-shaped clamp 290 such that C-shaped clamp 290, which is engaged with spinal rod 14, is translatable along tether 50. Hook portion 298 includes a grooved interior surface 299, as shown in FIG. 8. In some embodiments, surface 299 is smooth or even.

Tether 50 is engaged to bone screw 140, similar to bone screw 40 described herein. In one embodiment, as shown in FIG. 10, a head 142 of bone screw 140 includes a swivel 148 that rotates about an axis A2 such that head 142 is rotatable relative to a shaft 144, in the direction shown by arrows A. Swivel 148 has a disc-shaped configuration. In some embodiments, swivel 148 is variously shaped, such as, for example, those alternatives described herein. Swivel 148 includes an anchor 160 connected with end 56 of tether 50 that rotates tether 50 about an axis A3 relative to swivel 148, in the direction shown by arrows B. Anchor 160 includes a pair of spaced apart ends 162 fixed to swivel 148 and a post 164 disposed therebetween. Post 164 is rotatably engaged to ends 162. Tether 50 is connected to post 164 such that head 142 rotates tether 50 in a plurality of axial orientations relative to shaft 144. In one embodiment, as shown in FIG. 9, screw 148 does not include swivel 148 and anchor 160 comprises a first end including opening 161 and a second end including opening 163. A passageway 165 is disposed between openings 161 and 163. Openings 161, 63 and passageway 165 are configured for insertion and disposal of tether 50.

In operation, bone screw 140 is connected with end 56 of tether 50 via anchor 160. Bone screw 140 is connected with spinal tissue in a configuration for penetrating the spinal tissue. Bone screw 30 (FIG. 1) is connected with spinal tissue and spaced from bone screw 140. End 20 of spinal rod 14 is captured in cavity 294 of C-shaped clamp 290. Tether 50 is disposed in hook portion 298 of C-shaped clamp 290 and in cavity 268 of tensioning device 216. Ratchet 280 is engaged with tether 50.

A force is applied to arm 220, in the direction shown by arrow H, to engage teeth 281 of ratchet 280 with tether 50. Tether 50 is drawn through passageway 268 of tensioning device 216, in the direction shown by arrow G, such that tensioning device 216 translates relative to and along tether 50, in the direction shown by arrow I. The translation of tensioning device 216 along tether 50 engages tensioning device 216 with C-shaped clamp 290 to apply a force to C-shaped clamp 290, in the direction shown by arrow I. As tensioning device 216 draws tether 50 therethrough, tensioning device 216 translates C-shaped clamp 290, which is coupled with spinal rod 14, along tether 50 to dispose spinal rod 14 with bone screw 140. Releasing the force applied to arm 220 allows arm 220 to rotate from the first configuration to the second configuration. Arm 220 is repeatedly actuated and released until C-shaped clamp 290 is disposed with bone screw 140. The translation of spinal rod 14 along tether 50 disposes spinal rod 14 adjacent vertebrae at a surgical site for connection to the vertebrae, which applies a corrective force on vertebrae to selectively align vertebrae, as described herein. In some embodiments, tensioning device 216 is monolithically formed with, integrally connected or attached via fastening elements to C-shaped clamp 290.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a fastener comprising a shank configured for penetrating tissue and a head having a U-shaped inner surface that defines a passageway;
   a tether having an end connected to a concave portion of the inner surface such that the end is fixed to the fastener and disposed within the passageway;
   a spinal rod; and
   a reduction member connected with the spinal rod and engageable with the tether, the tether being connected to the spinal rod, the reduction member being translatable relative to the tether to dispose the spinal rod within the passageway.

2. A spinal construct as recited in claim 1, wherein the reduction member comprises a ratchet engageable with the tether.

3. A spinal construct as recited in claim 1, wherein the reduction member comprises a crimp that resists movement of the reduction member in at least one direction.

4. A spinal construct as recited in claim 3, wherein the crimp includes an inner surface having at least one penetrating element engageable with the tether to resist movement in the at least one direction.

5. A spinal construct as recited in claim 1, wherein the reduction member is translatable in a first axial direction and translation of the reduction member is resisted in a second axial direction.

6. A spinal construct as recited in claim 1, wherein the reduction member includes a connector defining a cavity configured for disposal of the spinal rod and coupling the spinal rod with the tether.

7. A spinal construct as recited in claim 1, wherein the spinal rod includes a first end attached with a bone screw configured to be fixed with vertebrae and a second end connected with the fastener.

8. A spinal construct as recited in claim 1, wherein the reduction member comprises a first inner surface that defines a cavity and a second inner surface that defines a passage, the spinal rod being disposed in the cavity and the tether being disposed in the passage, the first inner surface being spaced apart from the second inner surface.

9. A spinal construct as recited in claim 1, wherein the reduction member comprises a first inner surface that defines a cavity and a second inner surface that defines a passage that is spaced apart from the cavity, the spinal rod being disposed in the cavity and the tether being disposed in the passage.

10. A spinal construct as recited in claim 1, wherein the tether is resorbable.

11. A spinal construct as recited in claim 1, wherein the tether has a flexible configuration.

12. A spinal construct as recited in claim 1, wherein the tether has a rigid configuration.

13. A spinal construct as recited in claim 1, wherein the tether has a uniform thickness.

14. A spinal construct as recited in claim 1, wherein the reduction member comprises a first arcuate arm and a second arcuate arm, the arms defining a cavity therebetween, the cavity having the spinal rod positioned therein, the arms 15. A spinal implant system comprising:
- a fastener comprising a threaded shank configured for penetrating tissue and a head having a U-shaped inner surface defining a passageway;
- a tether having an end directly connected to a concave portion of the inner surface such that the end is fixed to the head, the tether extending away from the shank;
- an implant; and
- a reduction member connected with the implant and engageable with the tether such that the reduction member is movable in a first direction relative to the tether to translate the implant within the passageway and prevented from movement in a second direction.

16. A spinal implant system as recited in claim 15, wherein the reduction member comprises a tensioning device engageable with the tether.

17. A spinal Implant system as recited in claim 16, wherein the tensioning device includes a ratchet that draws the tether through the tensioning device.

18. A spinal construct comprising:
- a fastener comprising a shank configured for penetrating tissue and comprising a head having a U-shaped inner surface that defines a U-shaped passageway;
- a spinal rod;
- a tether comprising an end that is connected directly to a concave portion of the inner surface and disposed within the passageway, the tether extending away from the fastener such that the tether is coaxial with the fastener; and
- a reduction member comprising a cavity having the spinal rod disposed therein and a passage having the tether disposed therein, the tether being connected to the spinal rod, the cavity being spaced apart from the passage, the reduction member being translatable relative to the tether to dispose the spinal rod within the passageway.

19. A spinal construct as recited in claim 18, wherein the cavity extends perpendicular to the passage.

20. A spinal construct as recited in claim 18, wherein an end of the tether is directly connected to the fastener such that the end is fixed to the fastener within the passageway.

being movable relative to one another to expand and contract the cavity.

* * * * *

UNITED STATES PATENT AND TRADEMARK OFFICE
CERTIFICATE OF CORRECTION

PATENT NO. : 9,872,713 B2
APPLICATION NO. : 14/104131
DATED : January 23, 2018
INVENTOR(S) : Simpson et al.

It is certified that error appears in the above-identified patent and that said Letters Patent is hereby corrected as shown below:

On the Title Page

In Item (72), under "Inventors", in Column 1, Line 3, delete "Corodva, TN" and insert -- Cordova, TN --, therefor.

In the Specification

In Column 1, Line 63, delete "FIG, 7" and insert -- FIG. 7 --, therefor.

In Column 10, Line 60, delete "damp" and insert -- clamp --, therefor.

In Column 10, Line 62, delete "damp" and insert -- clamp --, therefor.

In Column 10, Line 64, delete "damp" and insert -- clamp --, therefor.

In Column 10, Line 66, delete "damp" and insert -- clamp --, therefor.

In Column 11, Line 1, delete "damp" and insert -- clamp --, therefor.

In Column 11, Line 4, delete "damp" and insert -- clamp --, therefor.

In Column 11, Line 6, delete "damp 290 such that C-shaped damp 290," and insert -- clamp 290 such that C-shaped clamp 290, --, therefor.

In Column 11, Line 27, delete "screw 148" and insert -- screw 140 --, therefor.

In Column 11, Line 30, delete "63" and insert -- 163 --, therefor.

Signed and Sealed this
Twenty-ninth Day of May, 2018

Andrei Iancu
*Director of the United States Patent and Trademark Office*